United States Patent [19]

Efthymiou et al.

[11] Patent Number: 4,861,483

[45] Date of Patent: Aug. 29, 1989

[54] APPARATUS AND PROCESS TO ELIMINATE DIFFUSIONAL LIMITATIONS IN A MEMBRANE BIOLOGICAL REACTOR BY PRESSURE CYCLING

[75] Inventors: George S. Efthymiou, Limassol, Cyprus; Michael L. Shuler, Ithaca, N.Y.

[73] Assignee: Cornell Research Foundation, Inc., Ithaca, N.Y.

[21] Appl. No.: 207,812

[22] Filed: Jun. 17, 1988

Related U.S. Application Data

[63] Continuation-in-part of Ser. No. 882,803, Jul. 7, 1986.

[51] Int. Cl.$^4$ ............................................. B01D 13/00
[52] U.S. Cl. ............................. 210/636; 210/321.69; 210/409
[58] Field of Search .................... 435/68, 174, 171; 210/636, 651, 409, 321.69

[56] References Cited

U.S. PATENT DOCUMENTS 4,769,150  9/1988  Ramstack .................. 210/321.69 X

OTHER PUBLICATIONS

Chibata et al, Ann. Rev. Biophys. Bioeng., 10:197 (1981).
Margaritis et al, CRC Crit. Rev. Biotechnical., 1:339 (1981).
Nagashima et al, Biotechnol. Bioeng., 26:992 (1984).
Wang, Ann. NY Acad. Sci., p. 313 (1983).
Kominek, Antimicrob. Agents Chemother, 7:856 and 861 (1975).
Finn, J. Ferm Technol., 44:305 (1966).
Brown et al, Euro. J. Appl. Microbiol. Biotechnol., 11:151 (1981).
Luong, Biotechnol. Bioeng., 27:280 (1985).
Aiba et al, Biotechnol. Bioeng., 10:845 (1968).
Holzberg et al, Biotechnol. Bioeng., 9:413 (1967).
Ghose, T. K. et al, Biotechnol. Bioeng., 21:1401 (1979).
Inloes, 1982 Ph.D. Thesis, Stanford University (pp. IV, V, 6, 7 and 8 only).
Vieth W. R. et al, Bioprocessing Technology, 8(3):8 (1986).
Choudhurg, J. P. et al, Biotechnology Letters, 8(10):731–734 (1986).
Cho, T. et al, Biotech. Prog., 2:53 (1986).
Finn, R. K., et al, ALS Symposium Series, 314,44 (1986).

Primary Examiner—Frank Spear
Attorney, Agent, or Firm—Jones, Tullar & Cooper

[57] ABSTRACT

An improved multilayer continuous biological membrane reactor and a process to eliminate diffusional limitations in membrane reactors in achieved by causing a convective flux of nutrient to move into and out of an immobilized biocatalyst cell layer. In a pressure cycled mode, by increasing and decreasing the pressure in the respective layers, the differential pressure between the gaseous layer and the nutrient layer is alternately changed from positive to negative. The intermittent change in pressure differential accelerates the transfer of nutrient from the nutrient layers to the biocatalyst cell layer, the transfer of product from the cell layer to the nutrient layer and the transfer of byproduct gas from the cell layer to the gaseous layer. Such intermittent cycling substantially eliminates mass transfer gradients in diffusion inhibited systems and greatly increases product yield and throughput in both inhibited and noninhibited systems.

21 Claims, 4 Drawing Sheets

APPARATUS AND PROCESS TO ELIMINATE DIFFUSIONAL LIMITATIONS IN A MEMBRANE BIOLOGICAL REACTOR BY PRESSURE CYCLING

This invention was made in part under JPL subcontract Grant No. 957240 for the Energy Conversion and Utilization technologies. The United States Government has certain rights to this invention.

This is a continuation-in-part application of co-pending application Ser. No. 882,803 filed July 7, 1986, which is incorporated herein by reference.

The present invention relates to an improved multimembrane biocatalyst cell bioreactor and process to eliminate diffusional limitations in such membrane reactors. More specifically, the invention relates to overcoming the feedback inhibition in such reactors by accelerating the transfer of nutrient from the nutrient layer to the biocatalyst cell layer, the transfer of product from the cell layer to the nutrient layer and the transfer of byproduct gas from the cell layer to the gaseous layer.

BACKGROUND OF THE INVENTION

Bioreactor studies have increasingly focused on immobilized cell systems [Chibata et al, *Ann. Rev. Biophys. Bioeng.*, 1981, 10: 197; Margaritis et al, *CRC Crit. Rev. Biotechnical*, 1: 339 (1981); Inloes, "Immobilization of Bacterial and Yeast Cells in Hollow-Fiber Membrane Bioreactors", 1982, Ph.D. Thesis, Stanford University; Nagashima et al, *Biotechnical, Bioeng.*, 26: 992 (1984)]. Possible improvements in productivity due to high cell densities has been a motivating factor. However, cell immobilization may not give increases of productivity in some systems due to feedback inhibition. In these cases integration of production and recovery in the same unit may be advantageous. The integration of bioconversion and separation to improve the productivity of a bioreactor has been considered, [Wang, *Ann. NY Acad. Sci.*, p. 313 (1983); Kominek, *Antimicrob. Agents Chemother*, 7: 856 and 861 (1971); Finn, *J. Ferm Technol.*, 44: 305 (1966], although few of these studies have focused on immobilized microbes. Since downstream product recovery is often a significant cost (both in money and energy), the challenge comes from not only the improvement of productivity in the bioreactor but also to reduce downstream processing costs.

The effects of feedback inhibition are well known, [Brown et al, *Euro. J. Appl. Microbiol. Biotechnol.*, 11: 151 (1981); Ghose et al, *Biotechnol. Bioeng.*, 21: 1401 (1979); Luong, *Biotechnol. Bioeng.*, 27: 280 (1985); Aiba et al, *Biotechnol. Bioeng.*, 10: 845 (1985); Holzberg et al, *Biotechnol. Bioeng.*, 9: 413 (1967)].

Heretofore the potential of immobilized or entrapped cell systems to greatly improve volumetric productivity in bioreactors has been limited, due in part, to the effects of diffusional limitations on nutrients or metabolic products. For example, if the desired product is inhibitory to its own formation and it can not be effectively transported away from the point of synthesis, the reaction will slow down or may even stop.

Various researchers have attempted to circumvent feedback inhibition and to integrate production and recovery: Wang, H. Y., *Ann. N.Y. Acad. Sci.*, 313: (1983); Kominek, L. A., *Antimicrob. Agents Chemother.*, 7: 856 and 861 (1975); Finn, R. K., *J. Ferm. Technol*, 44: 305 (1966); Choudhurg, J. P. et al., Biotechnology Letters, 8 (10): 731–734 (1986); Vieth W. R. et al, *Bioprocessing Technology*, 8 (3): 8 (1986).

Cho, T. and M. L. Shuler, *Biotech. Prog.*, 2: 53 (1986) described the operation of an immobilized cell multimembrane bioreactor, in which production and recovery were integrated. Finn, R. K., and Ercoli, E. (ALS Symposium Series, 314,44 (1986)), have used a simple two compartment reactor unit employing a hydrophilic membrane and cycling the presence in each compartment, to remove inhibitory acidic products formed by rumen bacteria.

Although many of these approaches are useful outside of the particle or unit immobilizing the cell mass, there is an unfilled need to minimize or reduce diffusional limitations in an entrapped or immobilized cell mass.

An improved membrane cell bioreactor and process that gives enhanced product yields in both feedback inhibited and nonfeedback inhibited systems is advantageous and would be adaptable to a wide range of biological cell reactions.

SUMMARY OF THE INVENTION

The reactor employed in this invention is an improvement of the reactor described in Patent Application Ser. No. 512,802, filed July 11, 1983, entitled "Continuous Biological Reactor" and in Application Ser. No. 882,803 entitled "Ethanol Production with Multi Membrane Bioreactor", both of which are hereby incorporated by reference.

One object of the present invention is an improved cell bioreactor and process wherein a convective flux of nutrient is caused to move into and out of an immobilized cell layer thereby eliminating diffusional limitations.

Another object of the invention is a multilayer biological membrane reactor useful for reacting a nutrient with a biocatalyst to form one or more biological products and gaseous by-products wherein said reactor comprises (1) a gaseous layer; an immobilized biocatalyst cell layer; and a nutrient layer; and (2) a means for sequentially causing a convective flux of nutrient to move into and out of the immobilized cell layer thereby (a) enhancing the production of biological product, its yield and its transfer from the cell layer into the nutrient layer via a semipermeable membrane separating the cell layer and nutrient layer and (b) causing the movement of gas from the gaseous layer into the biocatalyst cell layer and movement of gas and by-product gas, if any, out of the cell layer into the gaseous layer via a semipermeable membrane separating the biocatalyst cell layer from the gaseous layer; said rector optionally having additional layers, such as an extraction layer, to facilitate removal of product and by-product; wherein said means includes a means to effect a positive pressure differential between the gaseous layer and the nutrient layer; a means to change the pressure within one or more of the reactor layers to effect a negative pressure differential between the gaseous layer and the nutrient layer; and a means to alternately cycle between the positive pressure differential and the negative pressure differential.

A further aspect of the invention relates to the reactor adapted to operate in a continuous pressure cycled mode wherein in a first cycle the pressure in one or more layers is increased thereby creating a positive pressure differential between the gaseous layer and the nutrient layer, the reactant as in the gaseous layer is forced through the cell layer/gaseous layer membrane, usually a hydrophobic membrane, into the biocatalyst cell layer thereby displacing and forcing the nutrient and reactor product into the nutrient layer. The product can be isolated from the nutrient layer by various methods including transfer through a third semipermeable membrane into the extractant layer usually by means of product solubility in an extractive solvent contained in the extractant layer. In a second cycle the pressure in one or more layers is decreased creating a negative pressure differential between the gaseous layer and the nutrient layer. This reversal causes the nutrient layer to flow back into the cell biocatalyst layer while forcing the gas which entered the cell layer in the first cycle and by-product gas resulting from the reaction of the nutrient with the biocatalyst out of the cell layer and back into the gaseous layer. The complete cycle promotes the efficient contacting of the biocatalyst with nutrient and the intermittent removal and transfer of biological product and by-product gas away from the biocatalyst cell layer.

Another aspect of the invention is a process comprising a means for accelerating the movement of product from the vicinity of the biocatalyst in the biocatalyst cell layer and particularly a means for increasing the efficiency of the mass transfer of product by controlling intermittent cycling of the pressure in the gaseous layer and for overcoming feedback inhibition.

A further aspect of the invention is a process comprising the above described bioreactor coupled with a means for accelerating the movement of product generated in the biocatalyst cell layer by interaction of a biocatalyst and a nutrient first through a hydrophilic membrane into the nutrient layer and subsequently into a extractant or product layer by passage through a further semipermeable membrane separating the extractant layer and the nutrient-containing layer wherein said membrane may be either a hydrophobic membrane or a hydrophilic membrane depending on the specific bioreactor system.

DETAILED DESCRIPTION OF THE INVENTION

The present invention relates to an immobilized or entrapped multilayer bioreactor having at least three layers and preferably four layers (gas, biocatalyst cell layer, nutrient and extractant) which are separated by semipermeable membranes. More particularly the invention is a bioreactor and process having a means for overcoming the diffusional limitations of prior bioreactors whereby (1) the efficiency and rate of the mass transfer of product from cell reactor layer to nutrient layer is substantially increased, and (2) gaseous by-products, if any, are efficiently removed from the vicinity of the biocatalyst cells and pass through a semi-permeable membrane into the gaseous layer. The continuous removal of products and by-products prevents feedback inhibition and increases overall reaction rate and yield in both product inhibited and noninhibited systems.

The present invention is an improved cell bioreactor and process wherein a convective flux of nutrient is caused to move into and out of an immobilized cell layer thereby eliminating diffusional limitations in a biological membrane reactor comprising:

(a) a biocatalyst layer comprising a biocatalyst and a biological product formed by interaction between said biocatalyst and a nutrient; (b) a substrate layer sometimes referred to as a nutrient layer comprising a nutrient and a biological product; (c) a gaseous layer comprising one or more gaseous reactant nutrients and one or more gaseous by-products; and (d) an extraction layer comprising said biological product and extractant for said product; wherein (a) and (b) are separated from each other by means of a first membrane which is permeable to said nutrient and said biological product and impermeable to said biocatalyst; wherein (a) and (c) are separated from each other by a second semipermeable membrane which is permeable to said gaseous reactants and gaseous byproducts and impermeable to liquid and to said biocatalyst; whereby the biocatalyst and nutrient react to product the biological product, the biological product passes from the biocatalyst cell layer to the nutrient layer via the first membrane, the byproduct gas passes from the biocatalyst cell layer to the gaseous layer via the second membrane, the improvement which comprises a means for introducing a systemic convective flux of nutrient into and out of the cell layer thereby accelerating the transfer of nutrient from the nutrient layer to the biocatalyst cell layer, the transfer of product from the cell layer to the nutrient layer and the transfer of gaseous byproducts to the gaseous layer; wherein the convective flow of nutrient into and out of the biocatalyst layer is effected by establishing a positive and negative pressure differential between the gaseous layer and the nutrient layer and ntermittently cycling between the positive pressure differential and the negative pressure differential; wherein the pressure differential between the gaseous layer and the nutrient layer and said cycle is effected by regulating the pressure in the gaseous layer by sequentially opening and closing one or more valves in the gaseous layer, by regulating the pressure in the nutrient layer, or by controlling the pressure in both the gaseous layer and the nutrient layer.

In a preferred method such result is achieved by operating the reactor in a continuous pressure cycled mode. In a first cycle the gas pressure in one or more of the layers is increased creating a positive pressure differential between the gaseous layer and the nutrient layer thereby forcing the gas through a hydrophobic cell/gas membrane into the cell layer thereby displacing and forcing the product formed in the cell layer together with the substrate (nutrient) through a second membrane (hydrophilic) into the substrate or nutrient layer. The product subsequently passes from the nutrient layer through a third membrane (hydrophobic or hydrophilic) into an extractant layer from which the biological product can be isolated and/or continuously removed by various known methods such as by solubilization by a solvent present in the extractant (sometimes referred to as Extraction Layer).

The present invention includes a process for reacting a nutrient and reactant gas with a biocatalyst in an immobilized multilayer biological reactor to form one or more biological products and one or more byproduct gases which comprises:

(a) providing a multilayer biological membrane reactor as described in claim 3 which comprises a gaseous layer, and immobilized cell layer having an immobilized biocatalyst cell and a nutrient layer, all separated from one another by semipermeable membranes;

(b) charging the respective layers with reactant gas, a concentrated biocatalyst and nutrient to initiate a biocatalyst conversion of nutrient to biological product and byproduct gas;

(c) reacting the nutrient with biocatalyst and reactant gas to form biological product and byproduct gas;

(d) causing a systematic convective flow of nutrient to flow into and out of the biocatalyst layer thus accelerating the transfer of fresh nutrient from the nutrient layer to the cell layer, the transfer of product from the cell layer to the nutrient layer and the transfer of gaseous byproduct, if any, to the gaseous layer; and (e) isolating the biological product from the nutrient layer;

(f) wherein said flow of nutrient is achieved by a means to effect a positive pressure differential between the gaseous layer and the nutrient layer; a means to change the pressure within one or more of the reactor layers to effect a negative pressure differential between the gaseous layer and the nutrient layer; and a means to alternately cycle between the positive pressure differential and the negative pressure differential.

Heretofore the potential of immobilized or entrapped cell systems to greatly improve volumetric productivity in bioreactors has been limited, due in part, to the effects of diffusional limitations on nutrients or metabolic products. For example, if the desired product is inhibitory to its own formation and it can not be effectively transported away from the point of synthesis, the reaction will slow down or may even stop.

The instant invention relates to a modification of the multimembrane cell reactor and to a pressure cycling process that eliminates diffusion limitations. The new process increases reactor productivity by about an order of magnitude and in certain cases can eliminate the need for periodical nutrient additions.

Figure 1A:
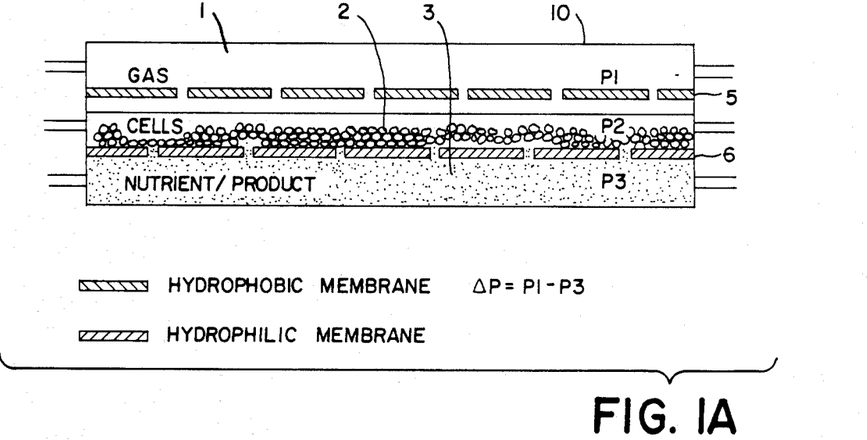
FIG. 1A is a schematic diagram of the multimembrane bioreactor showing the respective layers (gaseous layer 1; biocatalyst cell layer 2; nutrient or substrate layer 3; all separated by semipermeable membranes.

A suitable multimembrane immobilized biocatalyst cell reactor is schematically shown in FIG. 1A which incorporates three layers (1, 2, 3) separated by membranes 5 and 6. Additional layers may be used to further enhance reactor efficiency. A reactor having four layers separated by three membranes is schematically depicted in FIG. 1C. The top layer is the gas layer through which the gas byproduct produced during reaction is removed. A hydrophobic membrane separates the gas layer from the biocatalyst cell layer. The hydrophobic nature of the membrane enables it to allow gas to pass through it while blocking the passage of aqueous liquid for pressures below about 3 to 5 bars; however, the exact value of the critical entry pressure will vary from system to system and will depend on the properties of the specific membranes. The cell layer is separated from the third layer, which carries the nutrients, by a hydrophilic membrane. This membrane allows aqueous liquid to pass across it while it retains biocatalyst cells. The hydrophobic and hydrophilic membranes encompassing the biocatalyst cell layer must have pore sizes sufficiently small to retain the biocatalyst cells. The fourth (extractant) layer which carries the solvent, remove the product is separated from the nutrient layer by a hydrophobic membrane which is wetted by the solvent, filling the membrane pores. The solvent is prevented from passing through the membrane by maintaining a higher pressure on the aqueous nutrient side than the solvent side but lower than the critical entry pressure of the aqueous solution. One skilled in the art will recognize other methods for product removal.

The reactor and process is exemplified by the reaction of nutrient glucose to produce ethanol and carbon dioxide using *Saccharomyces cerevisiae* as immobilized biocatalyst cell layer. During operation of the reactor nutrients pass from the nutrient layer across the hydrophilic membrane into the biocatalyst cell layer where the biocatalyst cells take up glucose and produce ethanol and $CO_2$. The $CO_2$ produced cannot be carried out in solution because its production is rapid and its solubility in the aqueous solution is small. It passes through the hydrophobic membrane under a small pressure drop. The pressure in the cell layer must be higher, by the amount needed to remove the $CO_2$, than the pressure in the gas layer. If this is not the case, $CO_2$ accumulates in the cell layer and its pressure rises until it is enough to sustain the required flow of $CO_2$ through the membrane. When the $CO_2$ pressure in the cell layer rises above the pressure of the nutrient layer all the liquid in the cell ayer is pushed out by the $CO_2$. Therefore, the pressures should be controlled carefully to avoid the emptying of the liquid from the cell layer for prolonged periods of time. The ethanol (product) produced in the cell layer passes through the hydrophilic membrane into the nutrient layer and then through the hydrophobic membrane to the extractant (solvent) layer.

The allowable thickness of the cell layer is a critical parameter in the economic feasibility of the reactor. The thickness of the cell layer determines the amount of biocatalyst per unit membrane area in the reactor. This thickness is a function of the flux of nutrient such as glucose or ethanol (bioreactor product) across the nutrient membrane. When the reactor is operated in a "diffusional mode", substrates and products have to diffuse across the membrane and cell layer. The thickness of the cell layer that can be sustained in this case, is on the order of one millimeter. Because of such limitations on the amount of cells per unit membrane area, the potential for its economic competitiveness appears to be limited.

It has now been found that diffusion limitations can be eliminated by forcing the nutrients and products to flow across the hydrophilic membrane.

PRESSURE CYCLE MODE

The multimembrane reactor is operated in a mode that produces pressure driven flows across the hydrophilic membrane. By maintaining the pressure in the gas layer higher than the pressure in the feed layer, the gas passes through the hydrophobic membrane and forces the liquid in the biocatalyst cell layer out into the nutrient layer through the hydrophilic membrane. Even if all the liquid is removed from the cell layer the gas cannot easily pass the hydrophilic membrane and disrupt the reactor operation because of the high bubble pressure (ca. 2 bars). When the pessure in the nutrient layer is higher than the pressure in the gas layer liquid flows through the hydrophilic membrane into the biocatalyst cell layer. Liquid is prevented from going through the hydrophobic membrane because of its high entry pressure (ca. 3 bars). By alternately changing the pressure difference ($\Delta P$) between the gas and nutrient layers from positive to negative, liquid, nutrient is forced in and out of the immobilized cell layer. This operating strategy eliminates the concentration gradients across the hydrophilic membrane. With pressure cycling the concentration differences between the cell layer and the nutrient layer can be minimized.

The pressures needed to product the required liquid flow across the membrane depend on the membrane resistance to flow. The resistance depends on membrane properties such as pore size and porosity. Pore size is determined by the need for complete cell retention. The membrane must also have good mechanical strength. Because of the use of alternating hydrophobic and hydrophilic membranes exact pressure control is not critical. This facilitates ease of operation. The main constraint is that the duration of the pressure cycle and pressure differences should not allow the removal of liquid from the cell layer for an extended period of time. In such a case very high concentrations of inhibitor could build up fairly quickly.

An important aspect of the invention is to effect an intermittent cycling of fresh nutrient into an out of the biocatalyst layer to obtain substantially higher conversion at shorter reaction times than previously achieved by diffusion controlled process.

This is accomplished by establishing positive and negative pressure differentials between the pressure $P_1$ in the gaseous layer and the pressure $P_3$ in the nutrient layer. The criticality of selection of semipermeable membranes and respective pressure differentials ($\Delta P = P_3 - P_1$) are understood with reference to FIGS. 1A and 1B.

Figure 1B:
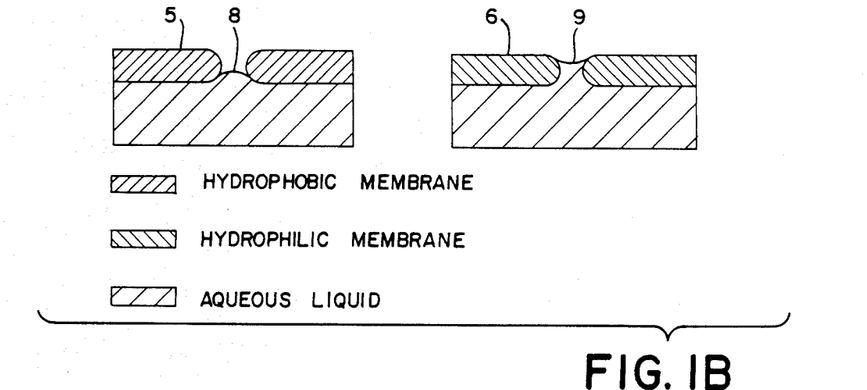
FIG. 1B shows hydrophobic membrane 5 which separates the gaseous layer 1 from the biocatalyst cell layer 2; a hydrophilic membrane 6 separates the biocatalyst cell layer 2 from the nutrient layer 3.
Figure 1C:
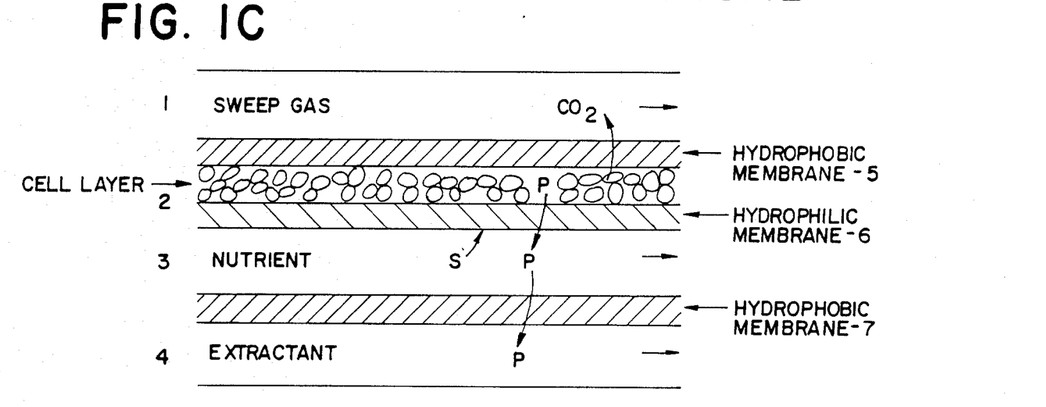
FIG. 1C shows a schematic diagram of the hydrophobic membrane 7 which separates the nutrient (substrate) layer 3 from the extractant (product) layer 4.

FIGS. 1A and 1B show the multimembrane reactor 10 with three layers. The gas layer is separated from the cell layer by a hydrophobic membrane 5. The cell layer is separated from the nutrient/product layer by a hydrophilic membrane 6. The pressures $P_1$, $P_2$ and $P_3$ represent the pressures in the gas, cell and nutrient/product layers respectively. During a pressure cycle sequence, initially in the pressure difference $\Delta P$ ($\Delta P = P_1 - P_3$) is made positive (i.e. the pressure in the gas layer is higher than the pressure in the nutrient/product layer). Under a positive pressure difference the gas from the gas layer enters the cell chamber through the hydrophobic membrane pores 8 and pushes the liquid in the cell chamber out through the pores of the hydrophilic membrane 6 into the nutrient product layer. When the desired amount of liquid has been forced out of the cell chamber, the pressure difference $\Delta P$ is made negative (i.e. the pressure in the nutrient/product layer is larger than the pressure in the gas layer). Under a negative $\Delta P$, liquid from the nutrient/product layer 3 is forced through the hydrophilic membrane 6 pores 9 into the cell chamber 2. The liquid entering the cell chamber 2, in turn forces the gas from the cell chamber out through the pores 8 of the hydrophobic membrane 5 into the gas layer 1 and out through the outlet from the gas layer.

When the desired amount of liquid enters the cell chamber 2 the pressure difference $\Delta P$ is again made positive and the cycle is repeated. The changing of the pressure difference from positive to negative and the exchange of gas and liquid to and from the cell chamber constitute the pressure cycle.

The pressure different $\Delta P$ can be made positive or negative by changing either the gas layer pressure, or the nutrient/product layer pressure, or both pressures, in a manner that will make $\Delta P$ positive or negative as required. FIG. 1B illustrates the characteristics of hydrophobic membranes 5 or 7 and hydrophilic membrane 6. The pores shown are idealized. When an aqueous liquid, (a liquid with a low contact angle) is in contact with a hydrophobic membrane near a pore, it will not penetrate the pore 8 without the application of a pressure that would force it through. The pressure required to force the liquid through the pore, called the "Liquid Entry Pressure" depends on properties of the pore and the liquid. These properties include the interfacial tension of the liquid and the liquid contact angle on the membrane material, the pore size and pore geometry. For a pore of 1 micron diameter this pressure is typically 3–5 bars.

In the case of a hydrophilic membrane 6 in contact with an aqueous liquid near a membrane pore 9, the liquid enters and fills the pore without the need to apply any pressure. To force the liquid out of pore 9, a pressure, called the "Bubble Pressure" has to be applied on the gas side of the pore. This pressure depends on the liquid interfacial tension, the liquid contact angle on the membrane material, the pore size and the pore geometry.

The pressure cycle operation of the multimembrane reactor is different from and does not resemble membranes flow-through reactors. As contrasted with the flow through reactor, the pressure cycled multimembrane reactor can supply gaseous nutrients to the cell layer and also remove any gaseous byproducts very effectively without being limited by the reactant gas or product gas solubilities in the nutrient product stream. These unique properties of the multimembrane reactor make it possible to operate an entrapped cell reactor without diffusion limitations. In addition, its unique spatial organization facilitates in situ product recovery through solvent extraction. The pressured cycled multimembrane reactor is an example of the use of membranes to achieve the significant advantages from their ability to compartmentalize a reactor and offer extra degrees of freedom in reactor design and operation.

The hydrophobic membrane separating the gas layer from the cell layer is optional. In a reactor configuration where this membrane is absent the cell layer/gas layer interface is controlled by a level controller. The interface is maintained between two fixed positions, an upper and lower, determined by the position of the level controller probes. The pressure cycle is effected through the liquid level controller. When the gas/cell layer interface is at the low point, the pressure in the gas layer is made lower tha the pressure in the nutrient/product layer. This lower liquid from the nutrient/product layer through the hydrophobic membrane into the cell layer. The cell layer/gas layer interface rises and when it reaches the high point the pressure in the gas layer is made higher than the pressure in the nutrient/product layer. This causes liquid from the cell layer to pass through the hydrophilic membrane into the nutrient/product layer, until the gas/cell layer interface reaches the low point again, where the cycle is repeated. The changes in pressure in the gas and nutrient/product layers can be achieved by linking the opening and closing of the valves in the respective layers to the level controller.

The extractant layer can vary with the process used. It can be a solvent or a resin, including ion exchange resin, that specifically adsorbs the product of interest. In such case, the resin does not have to be separated from the nutrient/product layer by a membrane. Rather, it can be placed in the nutrient/product stream. Other useful methods of product capture will be recognized by those skilled in the art.

The term entrapped biocatalyst cell refers to any biocatalyst which is confined to a particular area or layer of a multilayer biological reactor. The biocatalyst layer can be confined by a semipermeable membrane or by other means known in the art. Such confinement can be achieved by directly or indirectly controlling the level of the liquid or medium in which the biocatalyst resides by manipulating the various system or layer pressures. The term entrapped biocatalyst cell layer includes an immobilized biocatalyst cell layer but should not be construed to any one particular type thereof.

The term membrane reactor refers to a reactor having one or more membranes irregardless of how the biocatalyst cell layer is confined. The simplest system presently envisioned is one having a single semipermeable membrane separating a nutrient layer from a biocatalyst layer. A three-layer system, as shown in FIG. 1A includes a gaseous layer, a biocatalyst cell layer and a nutrient layer separated by two membranes. The reactor illustrated in FIG. 1C has four layers including an additional extractant layer and uses three membranes to define layer boundaries. Alternatively the membrane separating the gas and the biocatalyst layer may be eliminating by using a liquid level controller system to control the level of liquid in the biocatalyst layer. In such system the gas will be in direct contact with the liquid of the biocatalyst layer.

In the present invention, the term continuous process includes systems where the nutrient stream is passed through the reactor in a single pass and the nutrient is exhausted, and systems where a fraction of the nutrient stream is recycled with fresh nutrient added to make up for the nutrient consumed in the reactor.

ORGANISM

*Saccharomyces cerevisiae* ATCC #24858 (American Type Culture Collection Rockville Md.) was maintained on slopes of YM agar at 4° C. and used for the inoculum needed for the experiment. The organism was transferred to fresh media every three months.

MEDIA

The inoculum propagation medium consisted of: glucose 50 g; yeast extract 12 g; $(NH_4)_2SO_4$ 4.0 g; $KH_2PO_4$ 2.0 g; $MgSO_4.7H_2O$ 0.5 g; $CaCl_2.2H_2O$ 0.3 g; antifoam 15 mg; Deionized water 500 ml.

The fermentation medium composition used was: glucose 250 g; yeast extract 5 g; $(NH_4)_2SO_4$ 2.0 g; $KH_2PO_4$ 2.0 g; $MgSO_4.7H_2O$ 0.15 g; $CaCl_2.2H_2O$ 0.15 g; antifoam 30 mg; Deionized water 1000 ml.

ASSAYS

Glucose was analyzed by an enzymatic method (Calbiochem-Behring S.V.R. TM glucose test kit). The minimum value of glucose that can be measured is 2 mg/l with minor modifications. Reproducibility is ±5%.

Ethanol was also analyzed by an enzymatic method (Sigma Chemical Co., No. 322-UV EtOH Assay Kit). The assay of ethanol in TBP was also done with the same method. Minimum detectable concentration was about 3 mg/l and reproducibility was ±4%.

INOCULUM PREPARATION

Five hundred milliliters of inoculum propagation medium in a 1 liter Bellco flask was inoculated from a slope culture of YM agar medium and incubated at 35±1° C. and 250 rpm for 18 hours.

By "immobilized biocatalyst cell layer" is meant a plurality of organisms or microorganisms including plant and animal cells capable of reacting with a substrate or nutrient to form a biological product and byproduct and wherein said orgaisms are separated from other layers in a multilayer biological membrane reactor by means of semipermeable membranes essentially as shown in FIG. 1. The bioreactor in its simplest form is shown in FIG. 1A where cell layer 2 is separated from gaseous layer 1 by hydrophobic membrane 5 and from nutrient layer 3 by hydrophilic membrane 6. A more sophisticated bioreactor is shown in FIG. 1C which includes an additional extractant layer 4 separated from nutrient layer 3 by a hydrophobic membrane 7. Of course, it is understood that the choice of membrane type is not absolute but will depend on the particular bioreactor components, products and byproducts generated from the specific nutrients and specific biocatalyst cells. As used in this invention, the term "cells" or "biocatalyst cells" refers to organisms and microorganisms, including plant and animal cells, immobilized as noted above.

EXAMPLES

Figure 2:
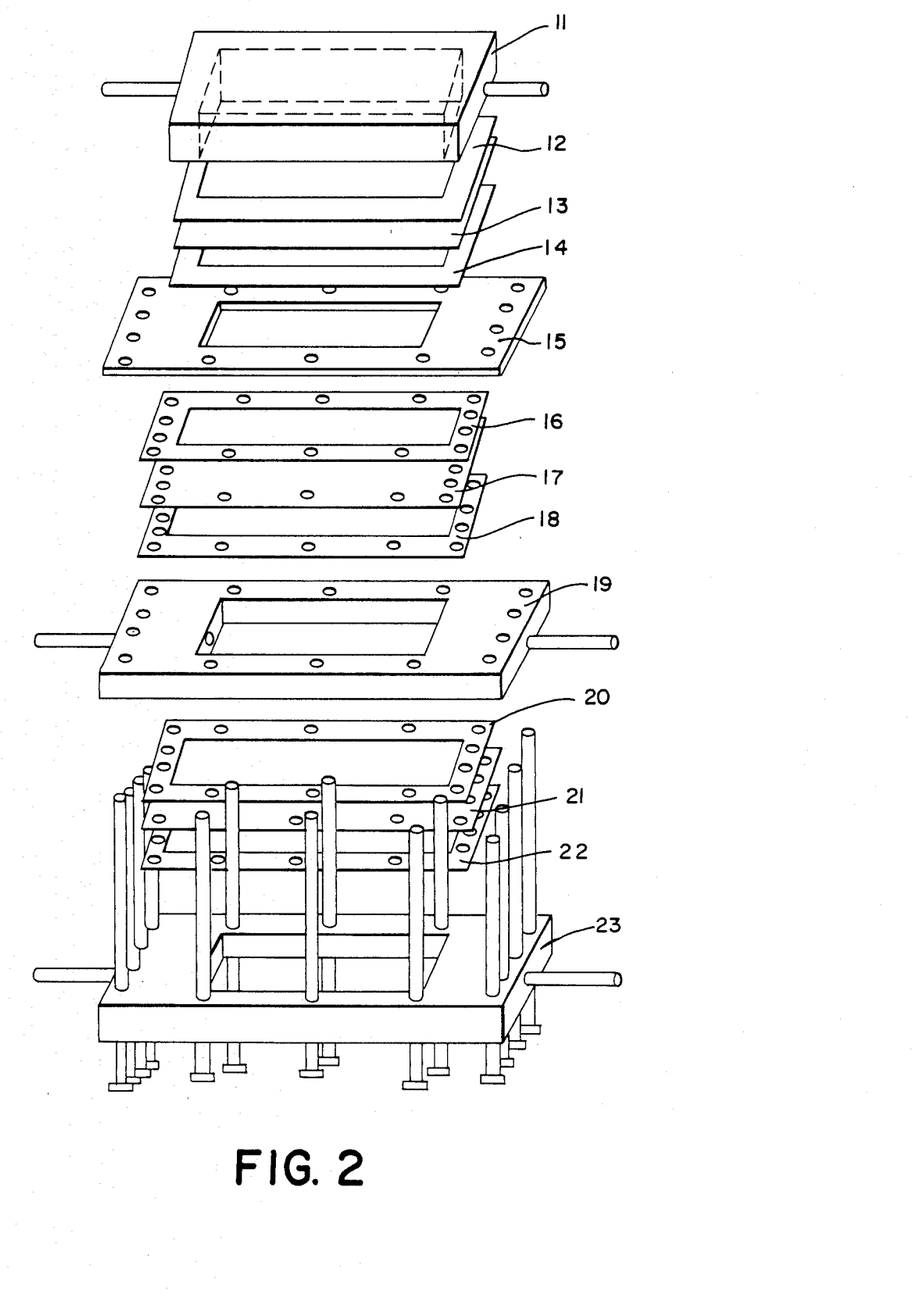
FIG. 2 is an exploded schematic of one type of bioreactor showing respective positioning from top down of gas chamber end plate (11); hydrophobic membrane (13) located between gaskets (12) and (14); cell chamber frame (15); hydrophilic membrane (17) located between gaskets (16) and (18); substrate (nutrient) feed chamber frame (19); hydrophobic membrane (21) between gaskets (20) and (22); and solvent end plate (23).
Figure 3:
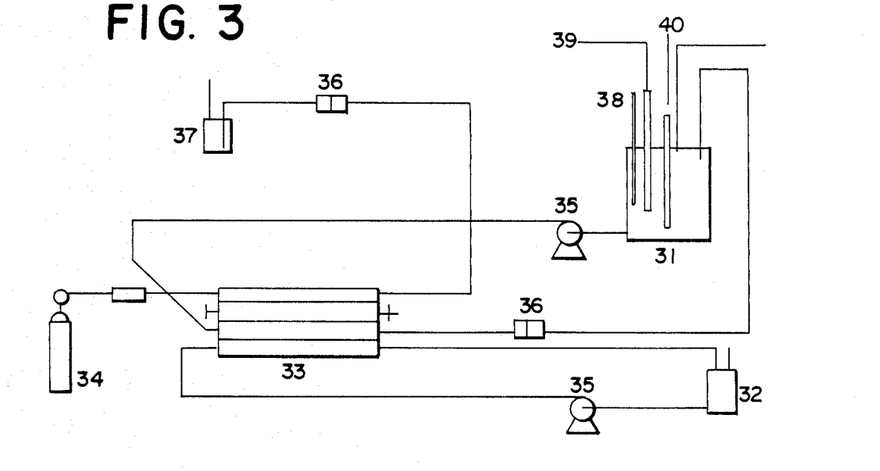
FIG. 3 is a schematic diagram of the pressure cycled bioreactor showing respective positioning of the nutrient recycle vessel (31); extractant recycle vessel (32); multimembrane reactor (33); gas cylinder (34); pump (35); solenoid valve (36); trap (37); thermometer (38); pH probe (39) and heater (40).

For these experiments the reactor of Cho and Shuler (Biotech, Prog., 2, 35, 1986) was modified as follows:

The cell and feed layers were separated by a polyvinylidene difluoride hydrophilic membrane from Millipore with a pore size of 0.22 μm. All the reactor frames had inlet and outlet tubes. The cell chamber was fifteen millimeters thick and had a volume of 200 ml. New gaskets cut out of silicone sheets were used and the membranes were sealed with high temperature silicone paste and allowed to harden. The cell chamber was filled with 200 ml of inoculum through the inlet tube. Air supplied from a gas cylinder was used as the sweep gas. The temperature was controlled by an electric resistance heater at 35° C. The pH was also controlled to 4.0 with a pH controller and a pH electrode. Samples were taken from both the cell layer and the recycle vessel as well as the TBP vessel every few hours and were stored in the refrigerator for later analysis. A schematic diagram of the bioreactor is shown in FIG. 1. The experimental system is depicted in FIG. 3. FIG. 2 is an exploded schematic drawing of the actual structure components of the bioreactor.

The pressure cycle control was achieved using an automatic timer and two solenoid valves. One valve opened and closed the gas layer outlet and the other did the same to the nutrient layer outlet. The valves opened and closed in alternate fashion with one valve open and the other closed at any time. The cylinder supply pressure was 12 psi and the maximum pump pressure was 7 psi. When the gas outlet valve was closed the pressure in the gas chamber rose to the value of the gas cylinder supply pressure forcing liquid out of the cell layer. At any time the feed outlet valve was closed and the other open, the pressure in the feed chamber reached the pump supply pressure, while the gas chamber pressure was very close to atmoshperic, therefore forcing liquid into the cell chamber. The pressure cycle time was equal to 2 minutes with 40 seconds for the emptying cycle and 80 seconds for the filling cycle. Other experiments have been run using cycles of about 20 seconds for filling and emptying. Of course the maximum length of the cycle will depend on the metabolic rate of the particular biocatalyst cell.

Two identical reactors were operated for these experiments. One was operated in the pressure cycle mode and the other was operated in the diffusion mode as a control. All the other conditions for the two reactors were exactly the same. The objective of the experiments was to demonstrate that the pressure cycle operation of the reactor vastly improved reactor performance. As a model system, ethanol production from glucose using Saccharamyces cerevisae was used. This system serves as a good model since it as been extensively studied in different reactors and the effect of feedback inhibition is known. The removal of ethanol was accomplished by solvent extraction from the reactor using tributyl phosphate (TBP).

Experiments were conducted comparing operation and results of the pressure cycle mode with the results obtained when the same reactor was operated in the normal prior art mode (diffusion controlled cycle). All the conditions for the two reactors were exactly the same except for the operating mode. The results are shown in FIGS. 4–9.

Figures 4, 5:
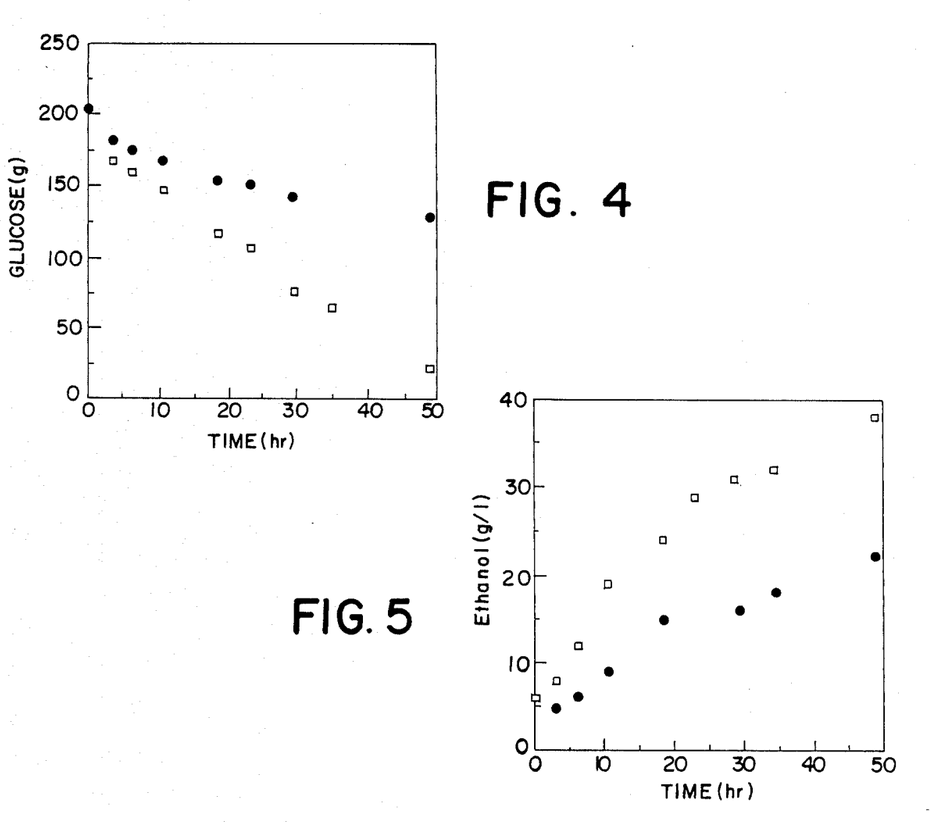
FIG. 4 is a plot of a total glucose (grams) consumpsion profile versus time (hours) comparing the diffusion controlled reactor (◆) with the pressure cycled reactor (□).
FIG. 5 is a plot of the ethanol concentration (grams/liter) in the recirculation vessel versus time (hours) comparing the diffusion controlled reactor (◆) with the pressure cycled reactor (□).

Referring to FIG. 4, almost all the glucose has been utilized in the pressure cycle reactor while very little was used in the diffusion controlled reactor (DCR). Table 1 shows that the growth in the pressure cycle reactor was double that of the diffusion controlled reactor. Additionally, while the initial cell viabilities are the same in both reactors the final viability in the DCR is significantly lower.

FIG. 5 shows the ethanol concentrations in the recirculation vessels for both reactors. There is considerable less ethanol in the DCR as would be expected from the glucose consumption noted above.

Figures 6, 7, 8, 9:
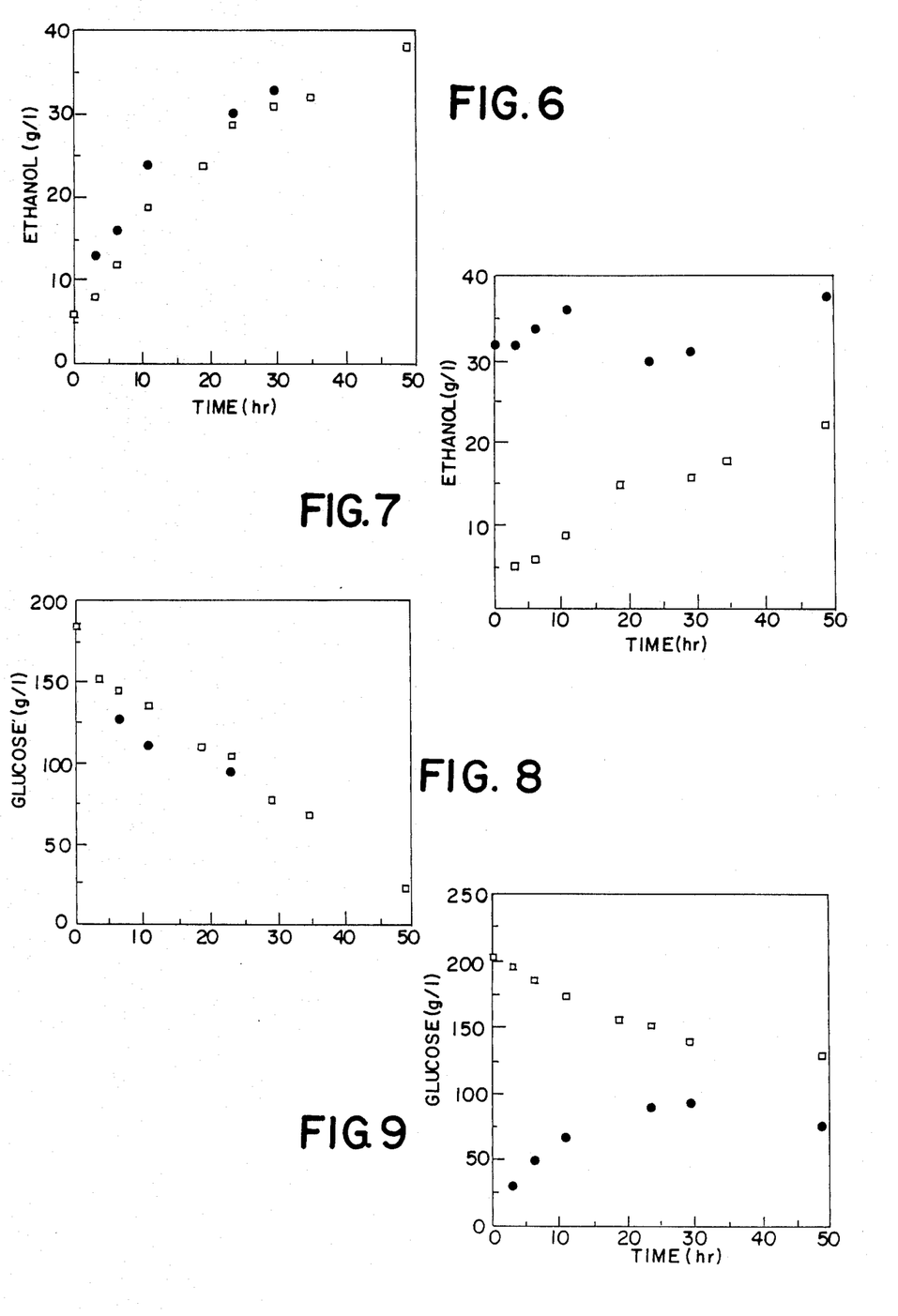
FIG. 6 is a plot of the ethanol concentration (grams/liter) versus time (hours) in the cell chamber (◆) and in the recirculation vessel (□) for the pressure cycled reactor.
FIG. 7 is a plot of the ethanol concentration (grams/liter) versus time (hours) in the cell chamber (◆) and in the recirculation vessel (□) for the diffusion controlled reactor.
FIG. 8 is a plot of the glucose (nutrient) concentration (grams/liter) versus time (hours) in the cell chamber (◆) and in the recirculation vessel (□) for the pressure cycled reactor ).
FIG. 9 is a plot of the glucose concentration (grams/liter) versus time (hours) in the cell chamber (◆) and in the recirculation vessel (□) for the diffusion controlled reactor.

In FIG. 8 the glucose concentration in the recirculation vessel and the cell chamber of the pressure cycle reactor are shown. There is little difference in the two concentrations indicating adequate flow across the membrane during the experiment. Similar results are shown in FIG. 6 that represents the ethanol concentrations with time, of the same reactor. FIG. 9 gives the glucose concentrations in the recycle vessel and cell chamber for the diffusion controlled reactor. Very large concentration gradients are apparent from FIG. 9. FIGS. 6 and 7 shows the vessel and cell chamber concentrations of ethanol for the pressure cycled reactor and the diffusion controlled reactor respectively. These data show that the ethanol concentration in the cell layer for the diffusion controlled reactor does not drop below the inoculum ethanol concentration; the ethanol concentration even increases initially. The consistently high ethanol concentration in the cell chamber of the diffusion controlled reactor appears to inhibit fermentation and lower the cell viability resulting in less glucose consumed and cell growth.

Since the inoculation procedure was identical for both reactors, the reaction began with the same concentration of ethanol. In the case of the pressure cycle reactor the ethanol concentration in the cell chamber dropped very quickly due to pressure cycling. For the diffusion controlled reactor however the ethanol concentration remained high.

The experimental results show very clearly the diffusion limitations are eliminated and reactor performance greatly enhanced by operation of the multimembrane reactor in a pressure cycling mode. No extra nutrients have to be added to the reactor during operation to complete the fermentation as is usually required with the diffusion controlled reactor.

Cell layer thickness is an important and critical parameter in the pressure cycled reactor. It determines the cell mass per unit membrane area in the reactor. The larger the cell mass per unit membrane area that can be sustained in the reactor, the larger the reactor productivity. Some cell growth in the cell layer would be desirable because it renews the cell mass and maintains high viability. This is particularly true for cells that have a limited lifespan as in the case of mammalian cells.

Table 1 compares the cell growth (grams per dry weight) and final viability for the Diffusion Controlled (Diff.) and Pressure Cycled (P.C.) reactors. It is seen that the cell mass (final and growth) is considerably greater for the Pressure Cycled Reactor. The cell growth in the diffusion controlled reactor was less than half the growth in the pressure cycle reactor. In addition, while the initial cell viabilities are the same in both reactors the final viability in the diffusion controlled reactor is significantly lower than in the pressure controlled reactor. As seen in Table 1 and FIGS. 4 to 9, the experimental results clearly demonstrate that operation of the multimembrane reactor in a pressure cycling mode eliminates diffusion limitations and markedly improves the biological reactor performance. It is noted that no extra nutrients had to be added to the reactor during operation to complete the ferementation as was required with the diffusional reactor. The final viability of the Pressure Cycled Reactor is 25 percent greater than for the Diffusion Controlled Reactor:

TABLE 1

Cell Growth and Final Viability in the Diffusion Controlled and Pressure Cycled Reactors

| Reactor | Cell mass (grams, dry wt.) | | | Viability % | |
|---|---|---|---|---|---|
| | Initial | Final | Growth | Initial | Final |
| Diff. | 1.8 | 2.7 | 0.9 | 98 | 60 |
| P.C | 1.8 | 3.9 | 2.1 | 98 | 85 |

What is claimed:

1. A multilayer biological membrane reactor comprising:
   (a) an entrapped biocatalyst cell layer and one or more additional layer including a gaseous layer, a nutrient layer and a product extractant layer all separated from one another by semipermeable membranes;
   (b) a means for introducing a systematic convective flux of gaseous and soluble nutrients to move into and out of the biocatalyst cell layer for accelerating the transfer of nutrient from the nutrient layer to the cell layer, the transfer of product from the cell layer to the nutrient layer and the transfer of gaseous byproduct, if any, to the gaseous layer.

2. The biological membrane reactor of claim 1 wherein said means comprises:
   a means to effect a positive pressure differential between the gaseous layer and the nutrient layer; a means to change the pressure within one or more of the reactor layers to effect a negative pressure differential between the gaseous layer and the nutrient layer; and a means to alternately cycle between the positive pressure differential and the negative pressure differential.

3. The reactor of claim 2 wherein the membrane separating the biocatalyst cell layer and the nutrient layer is a hydrophilic semipermeable membrane and the membrane separating the gaseous layer and the biocatalyst layer is a hydrophobic semipermeable membrane.

4. The reactor of claim 3 wherein the differential pressure and the pressure differential cycling is controlled by adjusting the inlet and outlet pressures in the gaseous layer.

5. The reactor of claim 3 wherein the differential pressure and the pressure differential cycling is controlled by adjusting the inlet and outlet pressures in the nutrient layer.

6. The reactor of claim 3 wherein the differential pressure and the pressure differential cycling is controlled by adjusting the inlet and outlet pressures in both the gaseous layer and the nutrient layer.

7. THe reactor of claim 3 wherein the pressures in the gaseous and nutrient layers and the cycle time depend on the nature and size of the biocatalyst, the product and the nature of the semipermeable membranes.

8. The reactor of claim 3 wherein the cycle time is from about 10 seconds to about 10 minutes.

9. A process for reacting a nutrient and reactant gas with a biocatalyst in an immobilized multilayer biological reactor to form one or more biological products and one or more byproduct gases which comprises:
   (a) providing a multilayer biological membrane reactor as described in claim 3 which comprises a gaseous layer, a cell layer having an immobilized biocatalyst cell and a nutrient layer, all separated from one another by semipermeable membranes;
   (b) charging the respective layers with reactant gas, concentrated biocatalyst and nutrients to initiate a biocatalyst conversion of nutrient to biological product and byproduct gas;
   (c) reacting the nutrient and reactant gas with biocatalyst to form biological product and byproduct gas,
   (d) causing a systematic convective flow of nutrient to flow into and out of the biocatalyst layer thus accelerating the transfer of fresh nutrient from the nutrient layer to the cell layer, the transfer of product from the cell layer to the nutrient layer and the transfer of gaseous byproduct, if any, to the gaseous layer; and
   (e) separating the biological product from the nutrient layer and the gaseous byproduct from the gaseous layer.

10. The process of claim 9 wherein the said process is a continuous process and the nutrient layer is treated to remove at least a portion of the biological product and recycled returning to the reactor.

11. The process of claim 10 wherein the convective flow of nutrient into andout of the biocatalyst layer is effected by alternately establishing a positive and negative pressure differential between the gaseous layer and the nutrient layer and intermittently cycling between the positive pressure differential and the negative pressure differential.

12. The process of claim 11 wherein the pressure differential between the gaseous layer and the nutrient layer and said cycle is effected by regulating the pressure in the gaseous layer by sequentially opening and closing one or more valves in the gaseous layer.

13. The process of claim 11 wherein the pressure differential between the gaseous layer and the nutrient layer and said cycle is effected by regulating the pressure in the nutrient layer by sequentially opening and closing one or more valves in the nutrient layer.

14. The process of claim 11 wherein the said pressure differential between the gaseous layer and the nutrient layer and said cycle is effected by controlling the pressure in both the gaseous layer and the nutrient layer.

15. The process of claim 9 wherein no membrane is used to separate the biocatalyst cell layer and the gaseous layer and the respective flows of nutrient, product and byproduct is effected by controlling the position of the interface between said layers.

16. In a multilayer biological membrane reactor comprising:
   (a) a biocatalyst cell layer comprising a biocatalyst and a biological product formed by reaction between said biocatalyst and a nutrient;
   (b) a nutrient layer comprising said nutrient and said biological product;
   (c) a gaseous layer comprising one or more gaseous reactants and one or more gaseous byproducts; and wherein (a) and (b) are separated from each other by means of a first membrane which is permeable to said nutrient and said biological product and impermeable to said biocatalyst; wherein (a) and (c) are separated from each other by a second semipermeable membrane which is permeable to said gaseous reactants and gaseous byproducts and impermeable to liquid and to said biocatalyst;

whereby the biocatalyst and nutrient react to produce the biological product, the biological product passes from the biocatalyst cell layer to the nutrient layer via the first membrane, the byproduct gas passes from the biocatalyst cell layer to the gaseous layer via the second membrane, the improvement which comprises a means for introducing a systematic convective flux of nutrient into and out of the cell layer thereby accelerating the transfer of nutrient from the nutrient layer to the biocatalyst cell layer, the transfer of product from the cell layer to the nutrient layer and the transfer of gaseous byproducts to the gaseous layer.

17. The reactor of claim 16 wherein said means comprises:
a means to effect a positive pressure differential between the gaseous layer and the nutrient layer; a means to reverse the pressure to effect a negative pressure differential between the gaseous layer and the nutrient layer; and a means to intermitently cycle in a definite time sequence the pressures in the respective layers to effect said pressure differentials.

18. The reactor of claim 17 wherein the first membrane is a hydrophilic semipermeable membrane and the second membrane is a hydrophobic semipermeable membrane.

19. The reactor of claim 18 wherein the pressure the gaseous layer and in the nutrient layer and the pressure differential between said layers is controlled by means of one or more valves in said layers and by means for opening and closing said valves.

20. The reactor of claim 16 having no membrane separating the biocatalyst cell layer and the gaseous layer thus allowing said layers to form an interface and having a means for controlling the position of the interface between a high liquid level and a low liquid level.

21. The reactor of claim 20 wherein said means is a liquid level controller operating on the liquid in the biocatalyst cell layer.

* * * * *

UNITED STATES PATENT AND TRADEMARK OFFICE
CERTIFICATE OF CORRECTION

PATENT NO. : 4,861,483

DATED : August 29, 1989

INVENTOR(S) : EFTHYMIOU et al

It is certified that error appears in the above-identified patent and that said Letters Patent is hereby corrected as shown below:

Claim 7, column 13, line 59, "THe" should be --The--.

Claim 9, column 14, line 7, "nutrients" should be --nutrient--.

Claim 11, column 14, line 27, "andout" should be --and out--.

Claim 19, column 16, line 7, after "pressure" insert --in--.

Claim 19, column 16, line 10, insert --a-- before "means".

Signed and Sealed this

Tenth Day of July, 1990

*Attest:*

HARRY F. MANBECK, JR.

*Attesting Officer*  *Commissioner of Patents and Trademarks*